(12) United States Patent
Boveja

(10) Patent No.: US 6,760,626 B1
(45) Date of Patent: Jul. 6, 2004

(54) APPARATUS AND METHOD FOR TREATMENT OF NEUROLOGICAL AND NEUROPSYCHIATRIC DISORDERS USING PROGRAMMERLESS IMPLANTABLE PULSE GENERATOR SYSTEM

(76) Inventor: Birinder R. Boveja, P.O. Box 210095, Milwaukee, WI (US) 53221

(*) Notice: Subject to any disclaimer, the term of this patent is extended or adjusted under 35 U.S.C. 154(b) by 294 days.

(21) Appl. No.: 09/942,322

(22) Filed: Aug. 29, 2001

(51) Int. Cl.⁷ .................................................. A61N 1/56
(52) U.S. Cl. ............................. 607/59; 607/60; 607/45
(58) Field of Search .......................... 607/1–3, 30–32, 607/59, 60, 45, 46, 48, 58

(56) References Cited

U.S. PATENT DOCUMENTS

| | | | |
|---|---|---|---|
| 3,311,111 A | * 3/1967 | Bowers | 607/30 |
| 3,623,486 A | * 11/1971 | Berkovits | 607/30 |
| 4,702,254 A | 10/1987 | Zabara | 128/421 |
| 4,867,164 A | 9/1989 | Zabara | 128/421 |
| 4,884,575 A | 12/1989 | Sanders | 128/419 PG |
| 5,304,206 A | 4/1994 | Baker et al. | 607/2 |
| 5,330,507 A | * 7/1994 | Schwartz | 607/14 |
| 5,391,188 A | * 2/1995 | Nelson et al. | 607/9 |
| 6,205,359 B1 | 3/2001 | Boveja | 607/45 |
| 6,622,041 B2 | * 9/2003 | Terry et al. | 607/9 |

* cited by examiner

*Primary Examiner*—George R. Evanisko

(57) ABSTRACT

System and method for neuromodulation therapy of neurological and neuropsychiatric disorders comprises an implantable lead and pulse generator system for providing the appropriate electrical stimulation to a cranial nerve such as the vagus nerve. The implantable pulse generator having prepackaged/predetermined programs stored in the memory of the pulse generator, and means for accessing these with an external magnet. The pulse generator adapted to selectively activate predetermined programs with the external magnet, thereby eliminating the need for an external programmer. The elimination of the external programmer resulting in significant cost reduction with essentially the same functionality.

14 Claims, 16 Drawing Sheets

(U.S. PATENT 5,304,206 - BAKER)

APPARATUS AND METHOD FOR TREATMENT OF NEUROLOGICAL AND NEUROPSYCHIATRIC DISORDERS USING PROGRAMMERLESS IMPLANTABLE PULSE GENERATOR SYSTEM

FIELD OF THE INVENTION

The present invention relates generally to implantable medical prostheses, more specifically, implantable pulse generator for treating or controlling neurological and neuropsychiatric disorders using pulsed vagal nerve stimulation.

The apparatus and methods disclosed herein also may be appropriate for the treatment of other conditions, as disclosed in co-pending application filed on Aug. 29, 2001, entitled APPARATUS AND METHOD FOR TREATMENT OF UROLOGICAL DISORDERS USING PROGRAMMERLESS IMPLANTABLE PULSE GENERATOR SYSTEM.

BACKGROUND OF THE INVENTION

Neuromodulation of cranial nerve using pulsed electrical stimulation has utility as an adjunct (add-on) therapy for neurological and neuropsychiatric disorders such as epilepsy, severe depression, dementia including Alzheimer's disease, compulsive eating disorders, sleeping disorder, coma, diabetes, neurogenic/psychogenic pain etc. This patent is directed to a system of implantable lead and pulse generator which is programmerless, and the pulse generator being controlled by only an external magnet.

Implanted pulse generator (IPG) for neuromodulation systems generally consist of an implantable lead, an implantable pulse generator, and an external programmer for non-invasively programming the parameters of the IPG. One such prior art is shown in FIG. 1.

The programmer generally is a microprocessor-based device, which provides a series of encoded signals to the implanted pulse generator by means of a programming head which transmits radio-frequency (RF) encoded signals to pulse generator according to the telemetry system laid out in that system. Such a system requires an antenna which is connected to input/output circuit for purposes of uplink/downlink telemetry through an RF telemetry circuit.

A built-in antenna enables communication between the implanted pulse generator and the external electronics (including both programming and monitoring devices) to permit the device to receive programming signals for parameter changes, and to transmit telemetry information, from and to the programming wand. Once the system is programmed, it operates continuously at the programmed settings until they are reprogrammed (by the attending physician) by means of the external computer and the programming wand.

In such a system any programming methodology may be employed so long as the desired information can be conveyed between the pulse generator and the external programmer.

Generally, implanted pulse generators work quite well, except their manufacturing costs and corresponding selling price tends to be high and places a burden on the health care system. A significant part of the cost is attributed to the programmability of the implanted device, as well as, the computer-based programmer itself.

Historically, implantable neurostimulator technology evolved based significantly on the existing cardiac pacemaker technology. Both are essentially electrical pulse generators. However, there is one significant difference, which is, for a cardiac pacemaker to function properly it needs to sense the electrical activity of the stimulating tissue. Therefore, in a cardiac pacemaker an external programmer is an integral part of the system to program the sensitivity. A system for nerve modulation is not dependent upon sensing from the stimulating tissue such as the nerve, before providing electric pulse stimulation.

Thus, by incorporating a limited number of predetermined/prepackaged programs into the implantable pulse generator, a significant manufacturing and development cost reduction for the system can be achieved, with very little loss of functionality.

BACKGROUND OF NEUROMODULATION

One of the fundamental features of the nervous system is its ability to generate and conduct electrical impulses. These can take the form of action potentials, which is defined as a single electrical impulse passing down an axon, and is shown schematically in FIG. 2. The top portion of the figure (A) shows conduction over mylinated axon (fiber) and the bottom portion (B) shows conduction over nonmylinated axon (fiber). These electrical signals will travel along the nerve fibers.

The nerve impulse (or action potential) is an "all or nothing" phenomenon. That is to say, once the threshold stimulus intensity is reached an action potential 7 will be generated. This is shown schematically in FIG. 3. The bottom portion of the figure shows a train of action potentials.

Most nerves in the human body are composed of thousands of fibers of different sizes. This is shown schematically in FIG. 4. The different sizes of nerve fibers, which carry signals to and from the brain, are designated by groups A, B, and C. The vagus nerve, for example, may have approximately 100,000 fibers of the three different types, each carrying signals. Each axon or fiber of that nerve conducts only in one direction, in normal circumstances.

In a cross section of peripheral nerve it is seen that the diameter of individual fibers vary substantially. The largest nerve fibers are approximately 20 $\mu$m in diameter and are heavily myelinated (i.e., have a myelin sheath, constituting a substance largely composed of fat), whereas the smallest nerve fibers are less than 1 $\mu$m in diameter and are unmyelinated. As shown in FIG. 5, when the distal part of a nerve is electrically stimulated, a compound action potential is recorded by an electrode located more proximally. A compound action potential contains several peaks or waves of activity that represent the summated response of multiple fibers having similar conduction velocities. The waves in a compound action potential represent different types of nerve fibers that are classified into corresponding functional categories as shown in the table below,

| Fiber Type | Conduction Velocity (m/sec) | Fiber Diameter ($\mu$m) | Myelination |
|---|---|---|---|
| A Fibers | | | |
| Alpha | 70–120 | 12–20 | Yes |
| Beta | 40–70 | 5–12 | Yes |
| Gamma | 10–50 | 3–6 | Yes |
| Delta | 6–30 | 2–5 | Yes |
| B Fibers | 5–15 | <3 | Yes |
| C Fibers | 0.5–2.0 | 0.4–1.2 | No |

The diameters of group A and group B fibers include the thickness of the myelin sheaths. Group A is further subdivided into alpha, beta, gamma, and delta fibers in decreasing order of size. There is some overlapping of the diameters of the A, B, and C groups because physiological properties, especially in the form of the action potential, are taken into consideration when defining the groups. The smallest fibers (group C) are unmyelinated and have the slowest conduction rate, whereas the myelinated fibers of group B and group A exhibit rates of conduction that progressively increase with diameter.

Compared to unmyelinated fibers, myelinated fibers are typically larger, conduct faster, have very low stimulation thresholds, and exhibit a particular strength-duration curve or respond to a specific pulse width versus amplitude for stimulation. The A and B fibers can be stimulated with relatively narrow pulse widths, from 50 to 200 microseconds ($\mu$s), for example. The A fiber conducts slightly faster than the B fiber and has a slightly lower threshold. The C fibers are very small, conduct electrical signals very slowly, and have high stimulation thresholds typically requiring a wider pulse width (300–1,000 $\mu$s) and a higher amplitude for activation. Because of their very slow conduction, C fibers would not be highly responsive to rapid stimulation. Selective stimulation of only A and B fibers is readily accomplished. The requirement of a larger and wider pulse to stimulate the C fibers, however, makes selective stimulation of only C fibers, to the exclusion of the A and B fibers, virtually unachievable inasmuch as the large signal will tend to activate the A and B fibers to some extent as well.

The vagus nerve is composed of somatic and visceral afferents and efferents. Usually, nerve stimulation activates signals in both directions (bi-directionally). It is possible however, through the use of special electrodes and waveforms, to selectively stimulate a nerve in one direction only (unidirectionally). The vast majority of vagus nerve fibers are C fibers, and a majority are visceral afferents having cell bodies lying in masses or ganglia in the skull. The central projections terminate largely in the nucleus of the solitary tract, which sends fibers to various regions of the brain (e.g., the thalamus, hypothalamus and amygdala).

Vagus nerve stimulation is a means of directly affecting central function. As shown in FIG. 6, cranial nerves have both afferent pathway 19 (inward conducting nerve fibers which convey impulses toward the brain) and efferent pathway 21 (outward conducting nerve fibers which convey impulses to an effector). The vagus nerve 54 is composed of 80% afferent sensory fibers carrying information to the brain from the head, neck, thorax, and abdomen. The sensory afferent cell bodies of the vagus reside in the nodose ganglion and relay information to the nucleus tractus solitarius (NTS).

FIG. 7 shows the nerve fibers traveling through the spinothalamic tract to the brain. The afferent fibers project primarily to the nucleus of the solitary tract (shown schematically in FIG. 8) which extends throughout the length of the medulla oblongata. A small number of fibers pass directly to the spinal trigeminal nucleus and the reticular formation. As shown in FIG. 8, the nucleus of the solitary tract has widespread projection to cerebral cortex, basal forebrain, thalamus, hypothalamus, amygdala, hippocampus, dorsal raphe, and cerebellum. In summery, it is these projections of the solitary track nucleus to the reticular system and other higher centers in the brain that is responsible for the therapy effects for neurological and neuropsychiatric disorders.

Prior Art

U.S. Pat. Nos. 4,702,254 and 4,867,164 (Zabara) are directed to neurocybernetic prosthesis, where an implantable pulse generator is controlled by an external programmer. The '254, and '164 patents on neurocybernetic prosthesis (NCP) point away from the present patent application since NCP utilizes neurocybernetic spectral discrimination by tuning the external current of the NCP generator to the electrochemical properties of a specific group of inhibitory nerves that affect the reticular system of the brain. According to the patent, the spectral discrimination analysis dictates that certain electrical parameters of the NCP pulse generator be selected based on the electrochemical properties of the nerves desired to be activated.

U.S. Pat. No. 4,884,575 (Sanders) is directed to a cardiac pacemaker adapted to generate a first pacing rate, and to selectively increase the rate to higher exercise rate which can be triggered with a time delay. In the Sanders patent, their is no suggestion to have a limited number of prepackaged/predetermined programs built into the pacemaker, and to selectively activate them with only a magnet. In a cardiac pacemaker, an external programmer is essential to adjust the sensitivity of the pacemaker, such that the pacemaker does not compete with the intrinsic rhythm of the heart.

In contrast, in the current patent application for neuromodulation of the vagus nerve in controlling neurological and neuropsychiatric disorders, there is no sensing involved from the stimulation tissue, i.e. the vagus nerve. Therefore, all of the stimulation programs containing the different electrical stimulation parameters, can be built-in, and which can be selectively activated with a magnet. This eliminates the need for an external programmer.

U.S. Pat. No. 5,304,206 (Baker et al) is directed to techniques and apparatus for activating implanted neurostimulators. In the Baker patent, as shown in FIG. 1, the implanted device communicates with a programmer and/or monitor external to the patient's body by means of asynchronous serial communication, to control and indicate device states. Further, the patient can adjust the implanted generator by finger tapping, whereby the piezoelectric sensor is activated. There is no suggestion in the Baker patent to simplify the implant by having prepackaged/predetermined programs in the implant, and eliminating the programmer.

U.S. Pat. No. 6,205,359B1 (Boveja) is directed to neuromoduation of a cranial nerve such as the vagus nerve for controlling neruologic disorders. The predetermined programs in the '359 patent, can be activated by manually pressing a button, since the pulse generator is external to the body.

SUMMARY OF THE INVENTION

A drawback of the prior art neuromodulation system is that it adds significant cost to the system. In the system of the current invention, high value is provided by eliminating the development of a computer based programmer to control the implanted pulse generator.

Accordingly, an apparatus and method of this invention comprises an implantable pulse generator and lead system which is adapted to provide pulsed electrical stimulation to a cranial nerve. The pulse generator comprises a limited number of predetermined/prepackaged programs built-in and means for accessing the programs with a magnet. The pulse generator also contains means to access the predetermined programs by a magnet. Thereby eliminating the need for an expensive computer based external programmer.

BRIEF DESCRIPTION OF THE DRAWING

For the purpose of illustrating the invention, there are shown in accompanying drawing forms which are presently preferred, it being understood that the invention is not intended to be limited to the precise arrangement and instrumentatlities shown.

DESCRIPTION OF THE INVENTION

The following description is of the current embodiment for carrying out the invention. This description is not to be taken in a limiting sense, but is made merely for the purpose of describing the general principles of the invention. The scope of the invention should be determined with reference to the claims.

Figure 1:
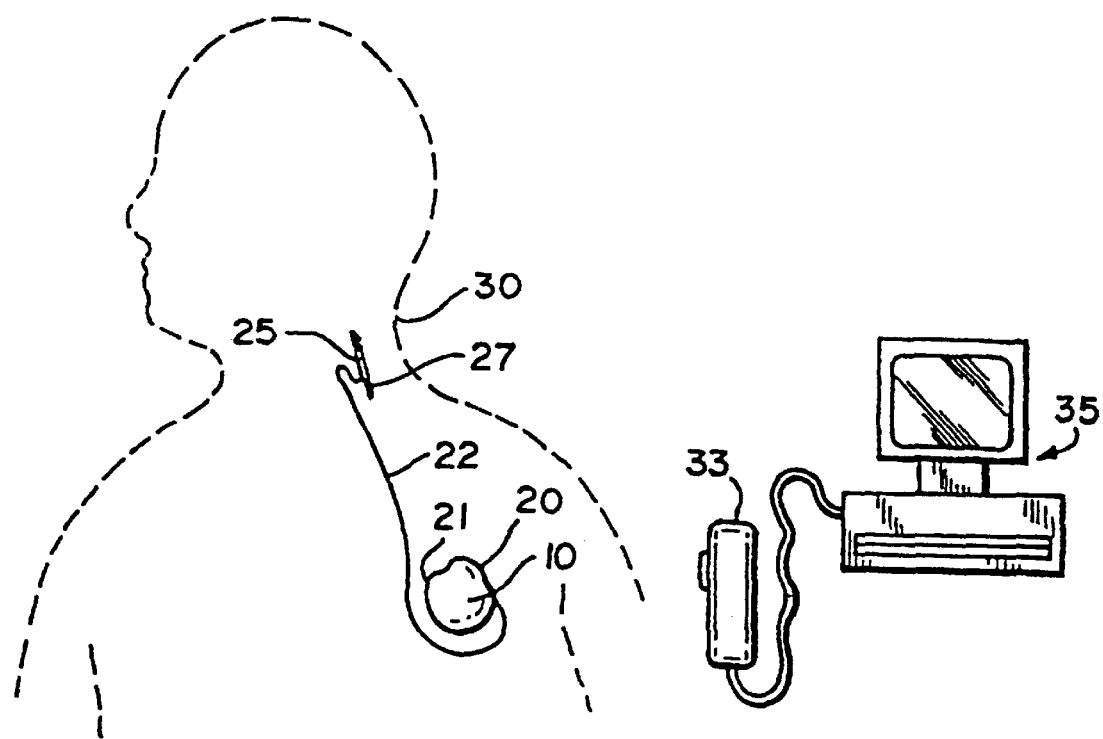
FIG. 1 is a schematic diagram of a prior art implantable pulse generator system with the programming controlled by an external personnel computer (PC) based programmer.
Figure 2:
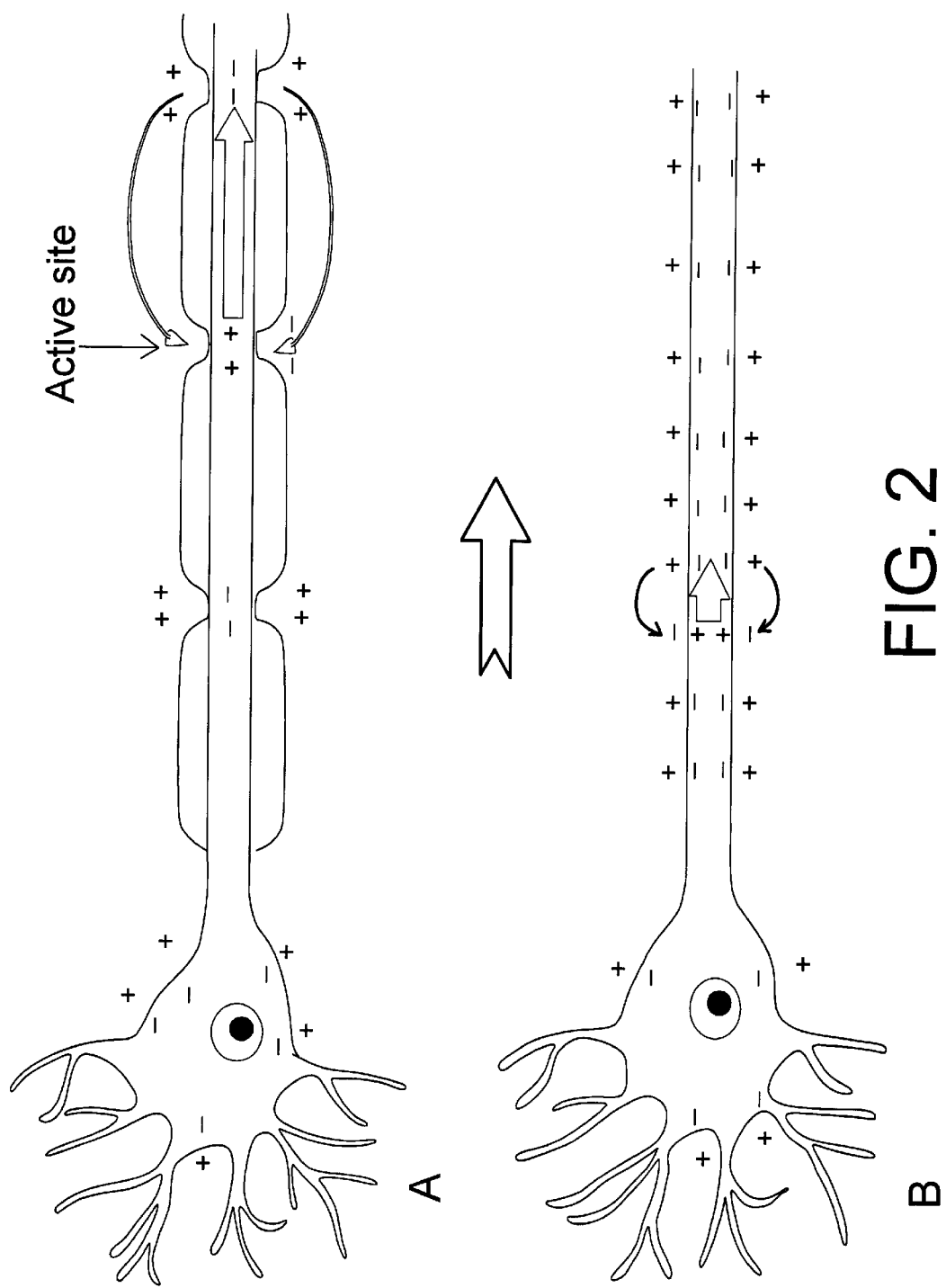
FIG. 2 is a schematic diagram of myelinated and nonmyelinated axon.
Figure 3:
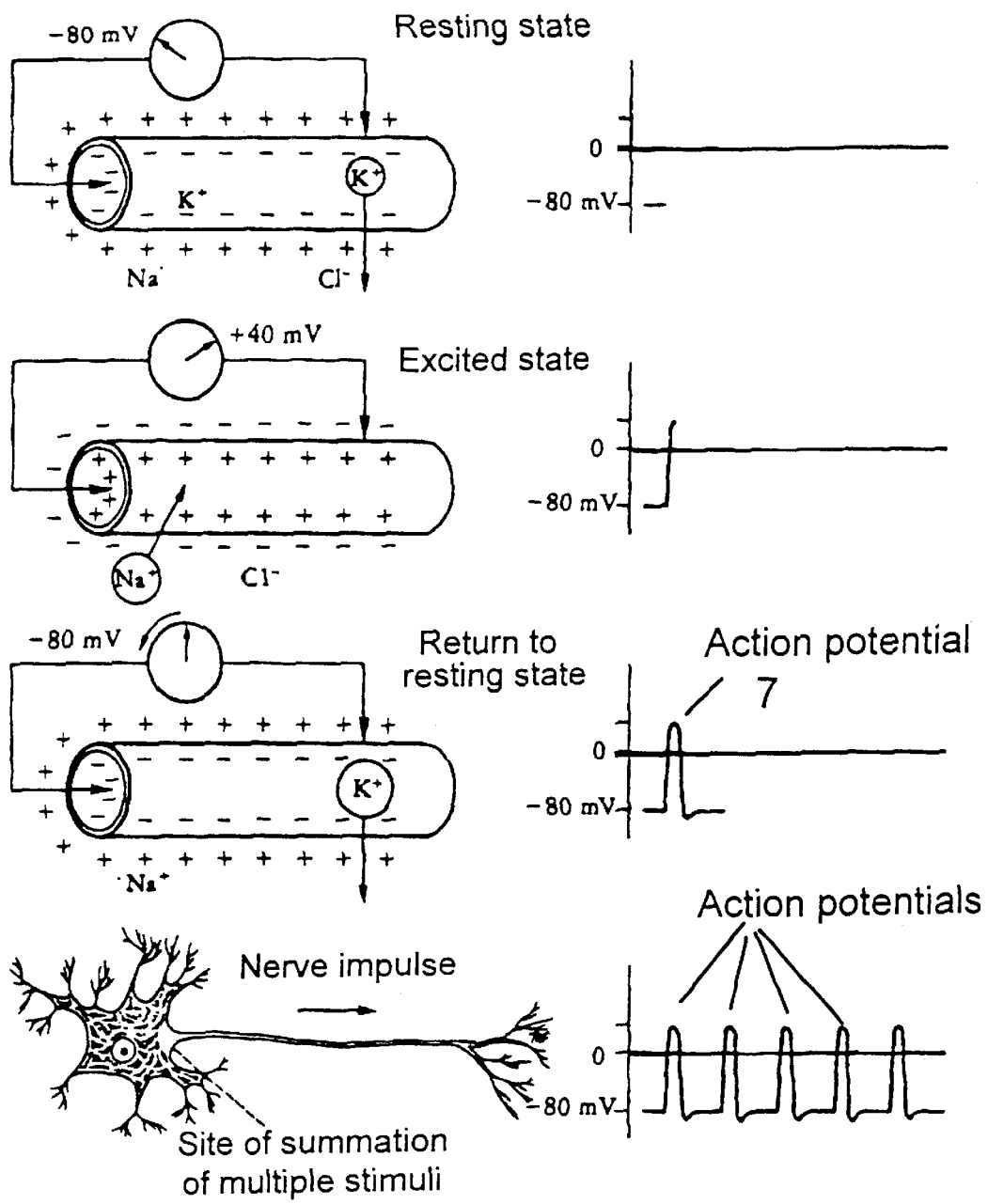
FIG. 3 is a schematic diagram of a single nerve impulse and a train of nerve impulses.
Figure 4:
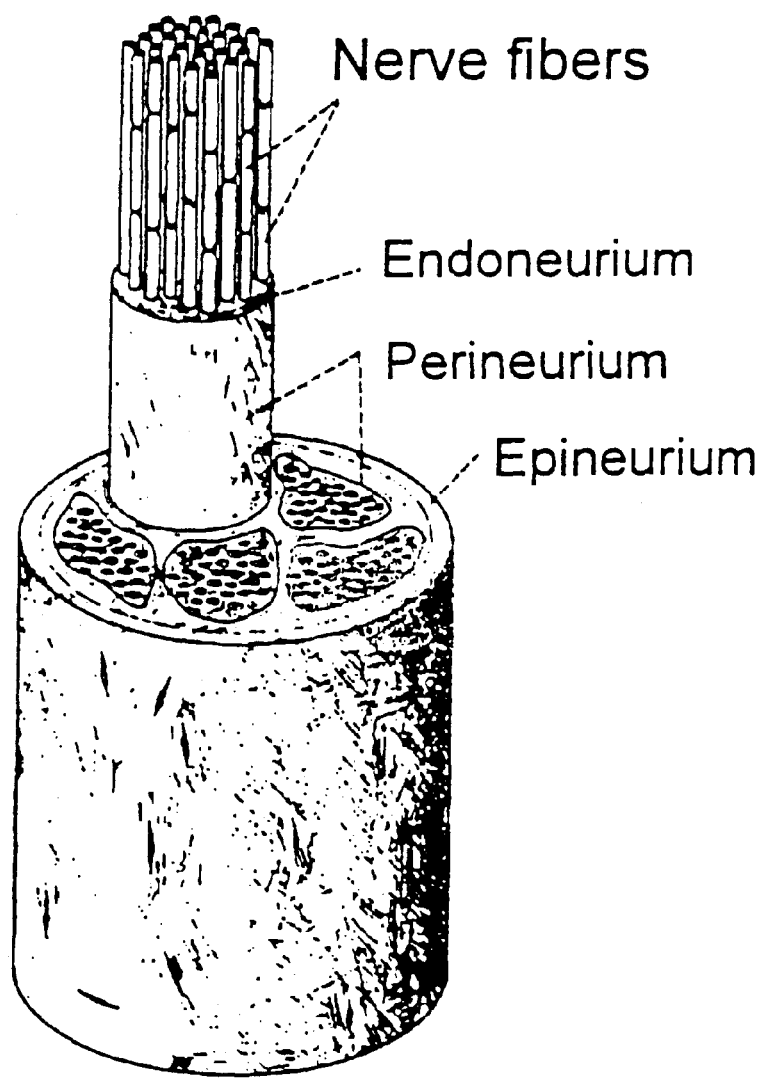
FIG. 4 is a diagram of the structure of a peripheral nerve.
Figure 5:
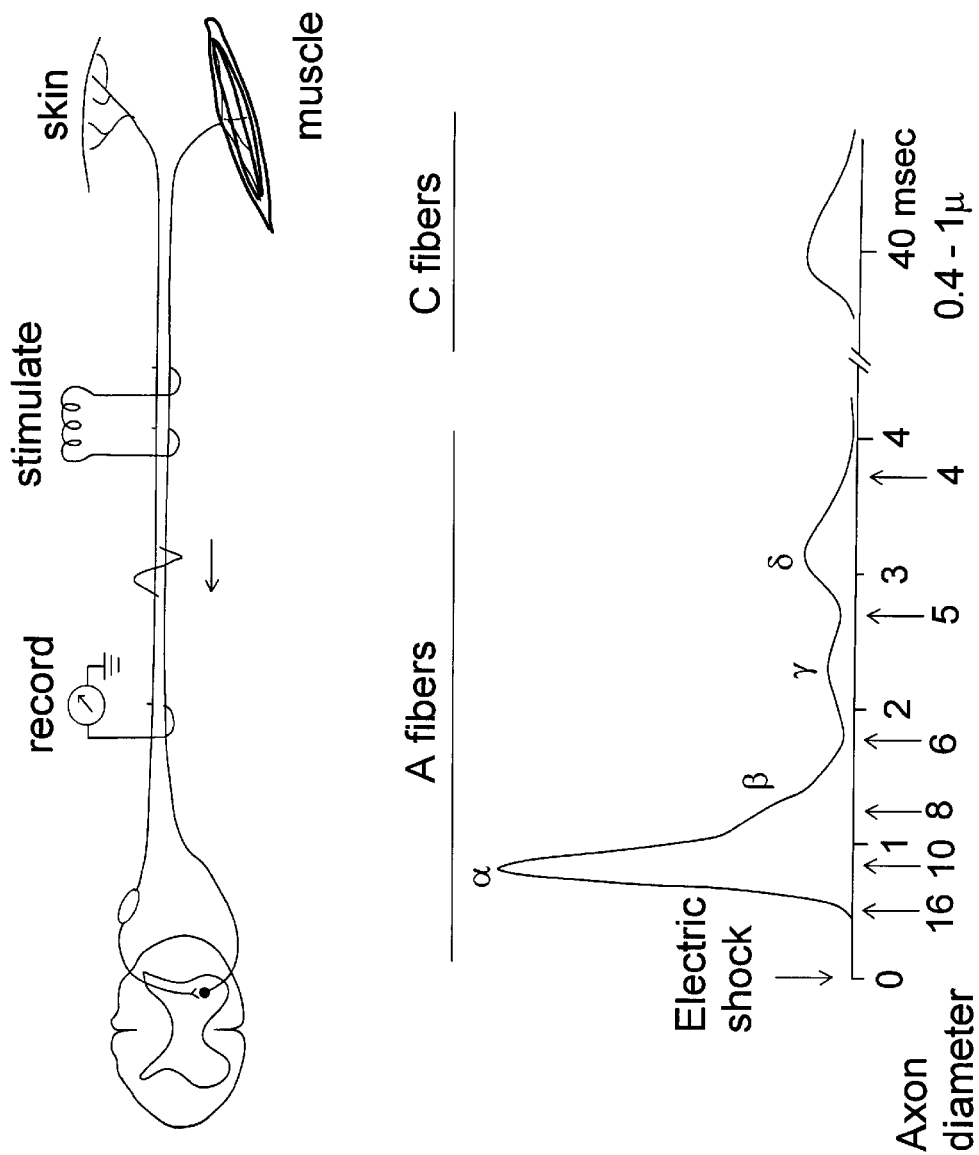
FIG. 5 is a diagram showing recordings of compound action potentials.
Figure 6:
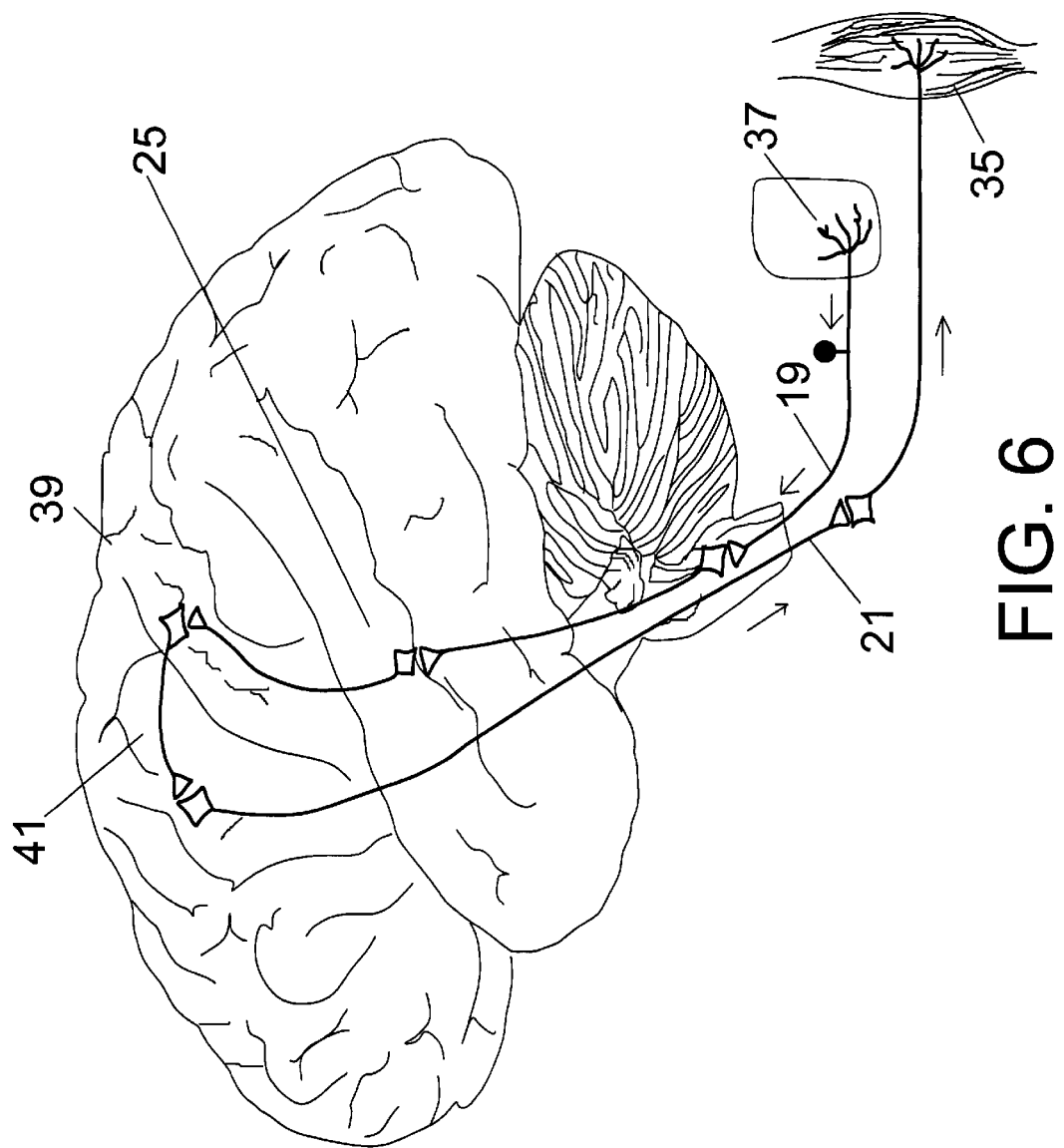
FIG. 6 is a schematic diagram of brain showing afferent and efferent pathways.
Figure 7:
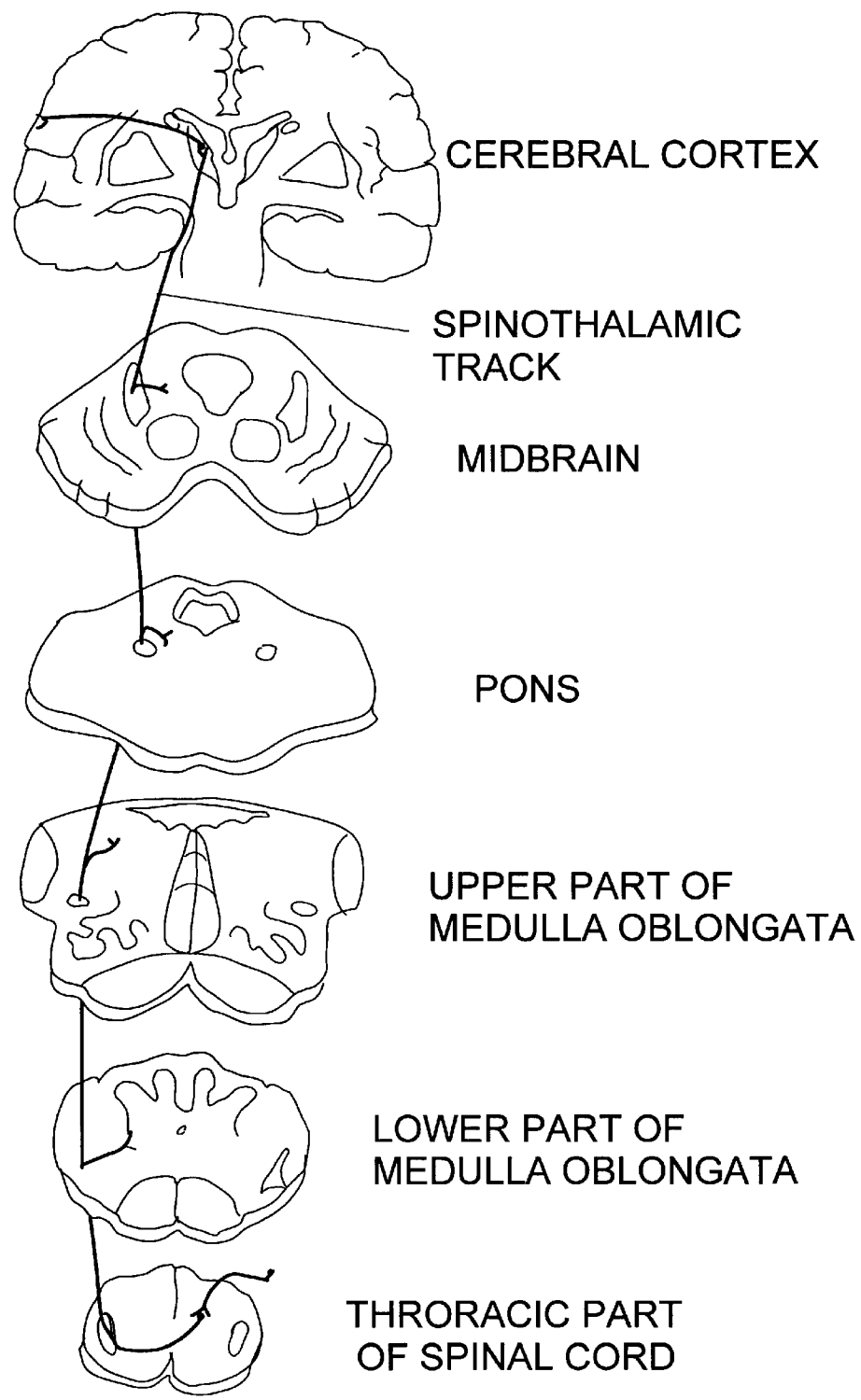
FIG. 7 is a schematic diagram showing pathways along the spinothalamic tract.
Figure 8:
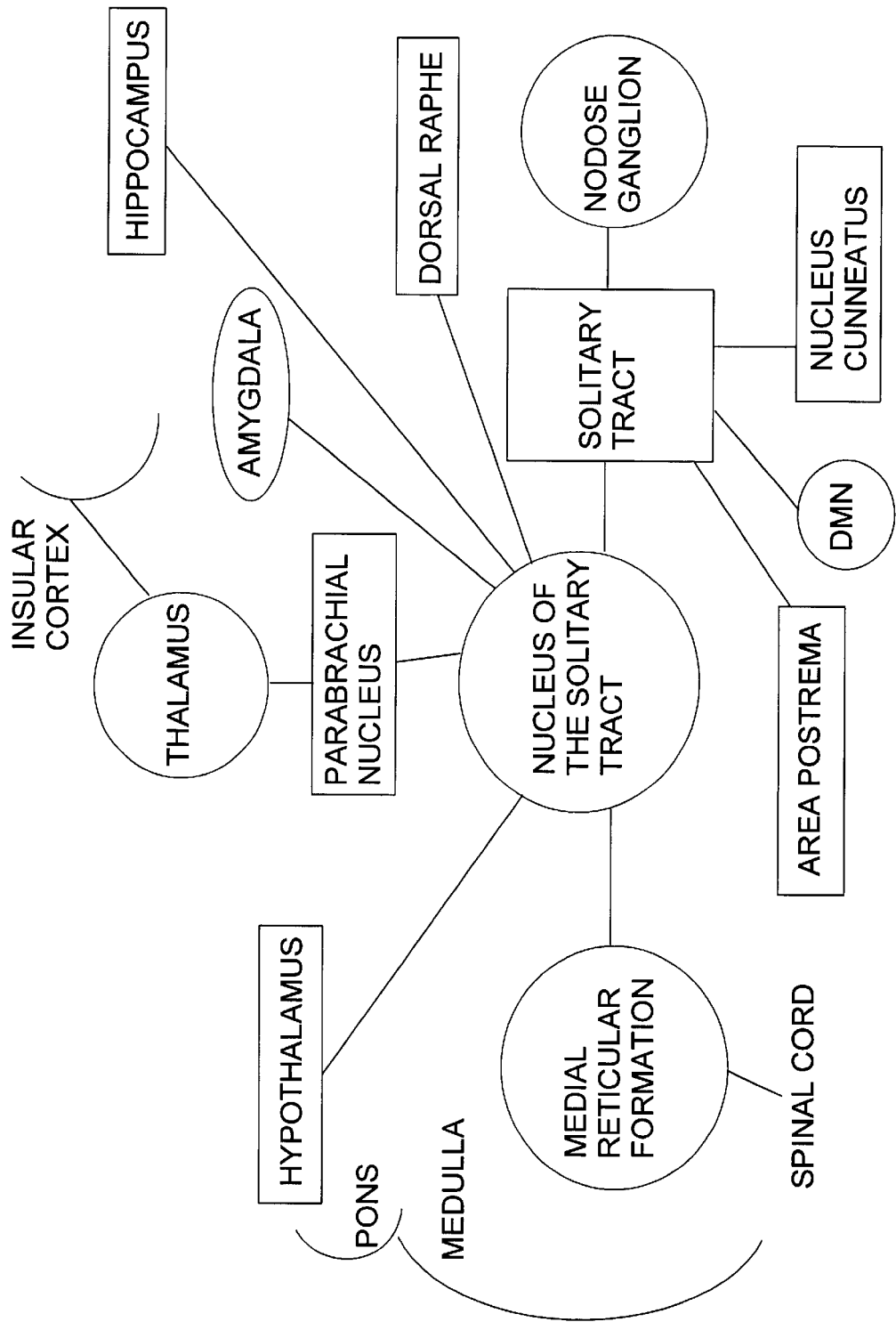
FIG. 8 is a schematic diagram showing relationship of Nucleus of the Solitary Track and how it relays information to other parts of the brain.
Figure 9:
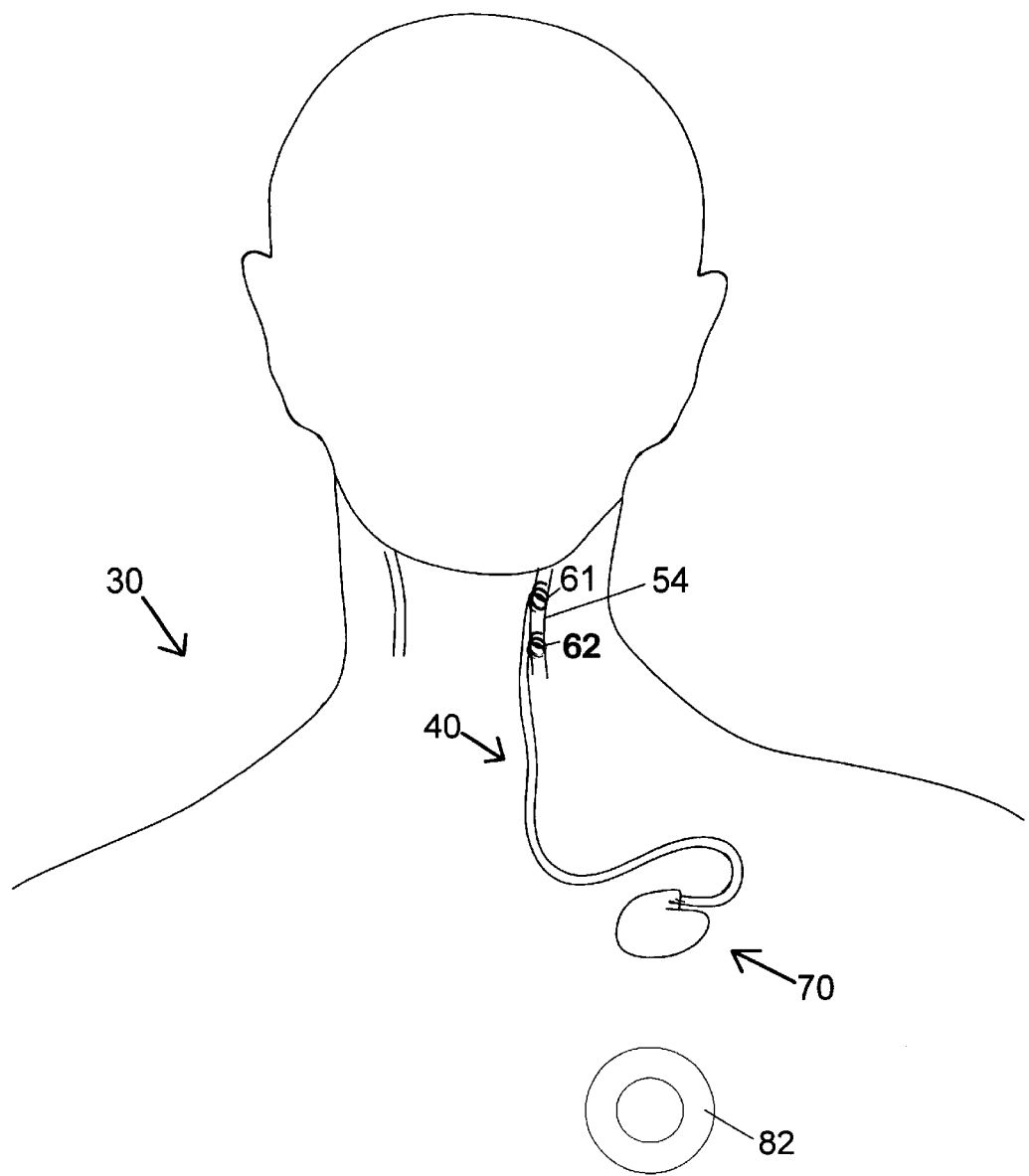
FIG. 9 is a schematic diagram of a patient with the implantable neurostimulator and lead with electrodes in contact with the vagus nerve.

Referring to FIG. 9, which shows a schematic diagram of a patient 30, with an implanted pulse generator 70 and an implanted lead 40 with a pair of electrodes 61,62 around the left vagus nerve. An external magnet 82 is the only device that controls the functioning of the pulse generator 70, as the predetermined/pre-packaged programs are preloaded within the implanted pulse generator 70.

Figure 10:
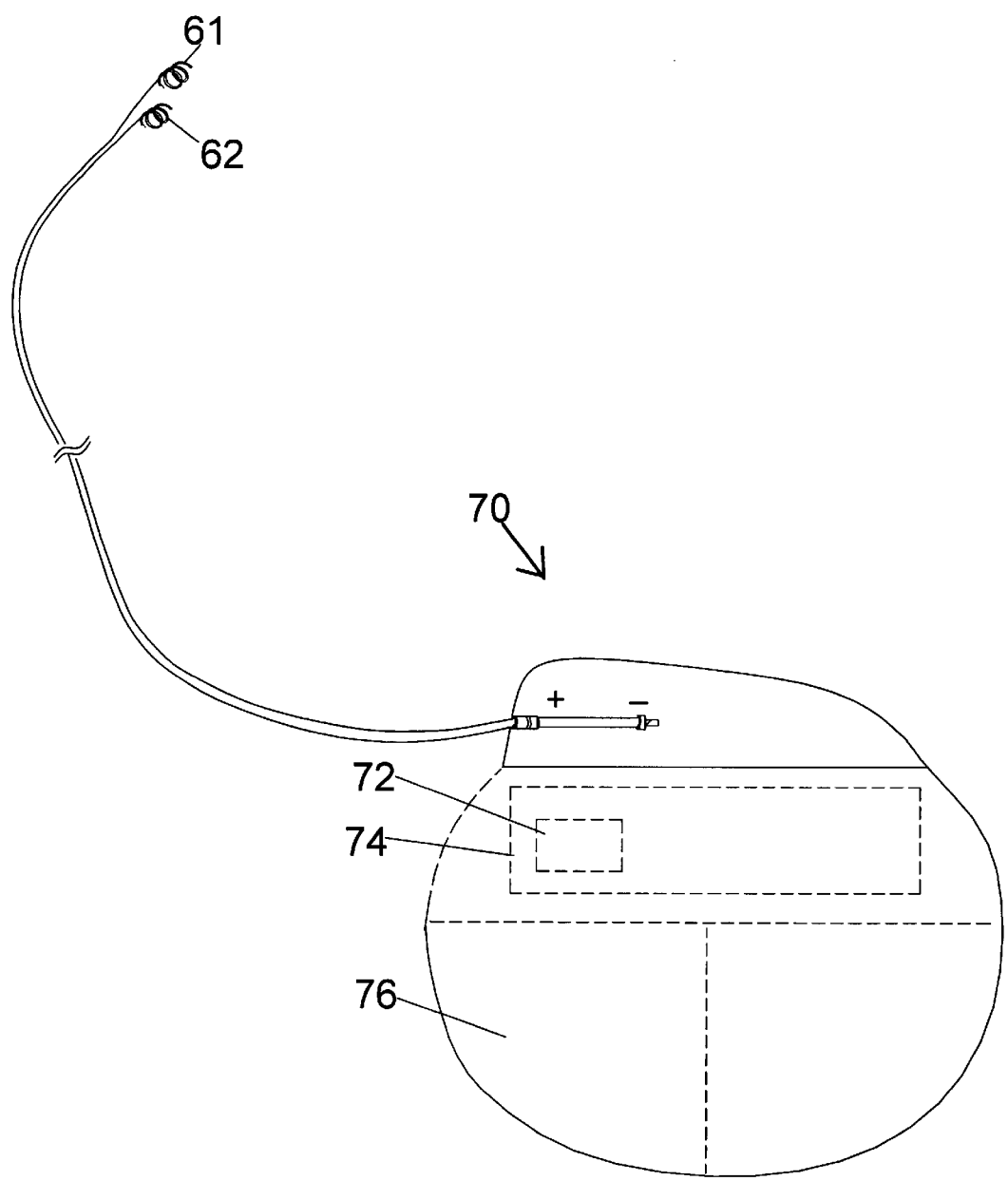
FIG. 10 is a close-up of the implantable neurostimulator system.

FIG. 10 shows the basic elements of the implantable pulse generator (IPG) system, that are well known in the art. The output of the pulse generator 70 is delivered to the vagus nerve 54 of a patient 30 via two electrodes 61,62 in contact with the vagus nerve 54. The conductors (not shown) connecting the electrodes 61,62 to the pulse generator 70 are insulated from each other and from the body tissues and fluids by material made of either medical grade silicone or polyurethane. The hybrid circuitry 74 containing a microprocessor 72 is driven by Lithium batteries 76, preferably Lithium Thionyl Chloride.

Electronic circuitry and batteries are encased in a titanium can which is punched from titanium sheet. Housing is made of titanium because it is biologically compatible and the pulse generator case is hermetically sealed utilizing laser welding techniques standard in the art.

Figure 11:
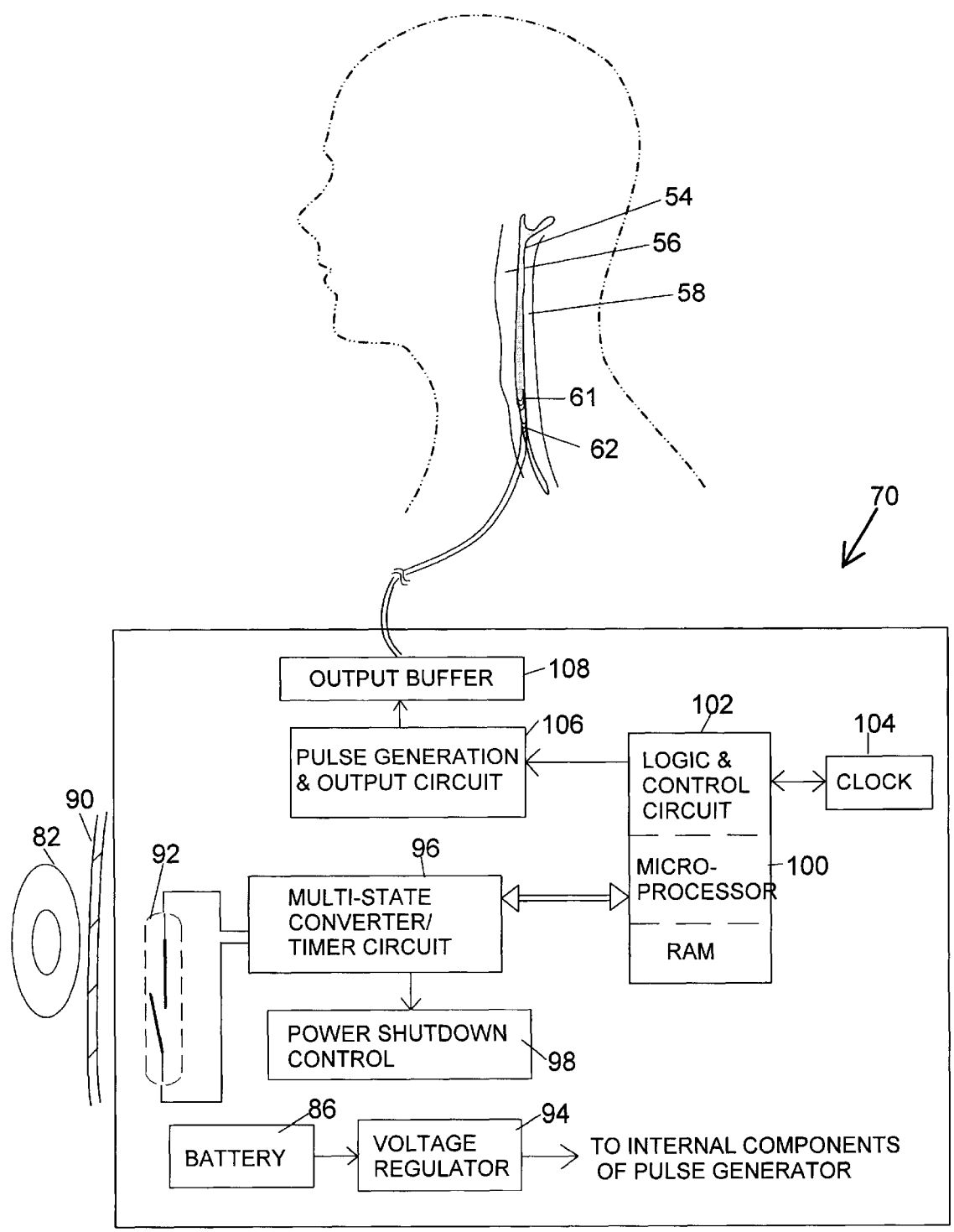
FIG. 11 is a simplified block diagram showing control of the implantable neurostimulator with a magnet.

Referring now to FIG. 11, the implantable pulse generator 70 is provided with a reed switch 92 and memory circuitry. The reed switch 92 being remotely actuable by means of a magnet 82 brought into proximity of the pulse generator 70, in accordance with common practice in the art. In this embodiment, the reed switch 92 is coupled to multi-state converter/timer circuit 96, such that a single short or prolonged closure of the reed switch can be used as a means for non-invasive encoding and programming of the pulse generator 70 parameters.

Figure 12:
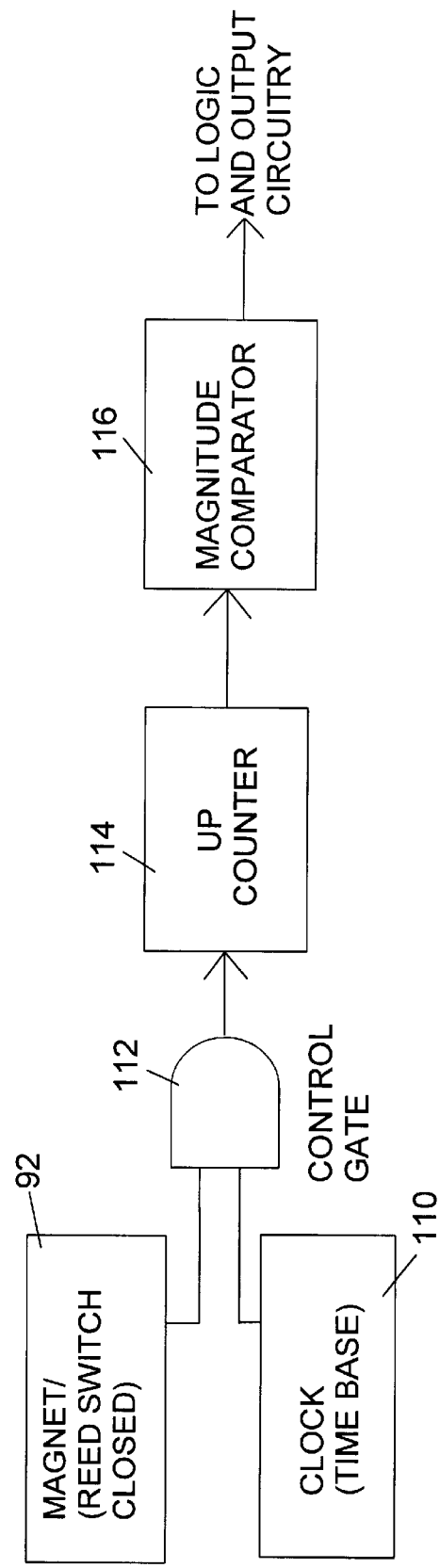
FIG. 12 is a schematic diagram showing implementation of a multi-state converter.

The closing of the reed switch 92 triggers a counter. As shown in FIG. 12, the magnet and timer are ANDed together. In the presently preferred embodiment, the system is configured such that during the time that the magnet 82 is held over the pulse generator 70, the output level goes from LOW stimulation state to the next higher stimulation state every 5 seconds. Once the magnet 82 is removed, regardless of the state of stimulation, an application of the magnet, without holding it over the pulse generator 70, triggers the OFF state, which also resets the counter.

Figure 13:
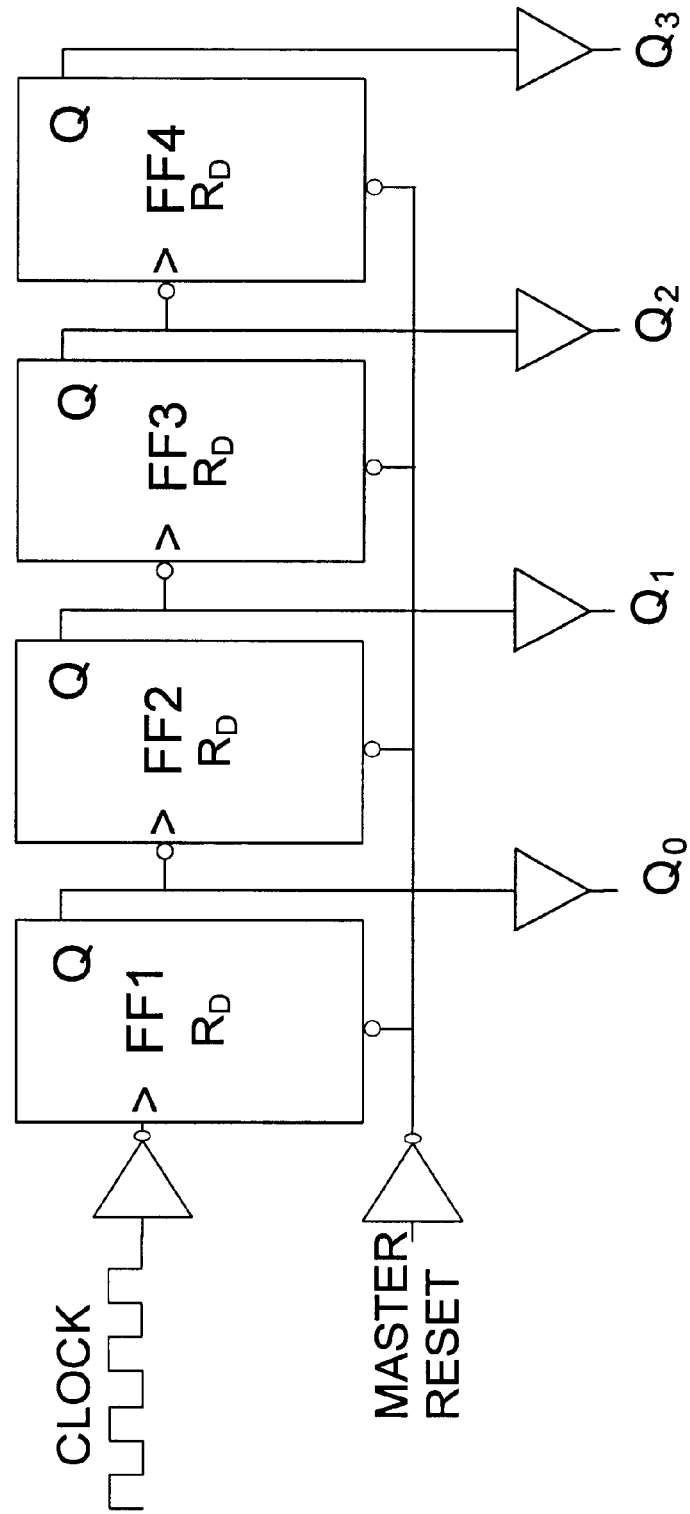
FIG. 13A is a logic diagram of a 4 bit counter.
FIG. 13B is a synchronous up-counter with 3 J-K flip flops.
Figure 13:
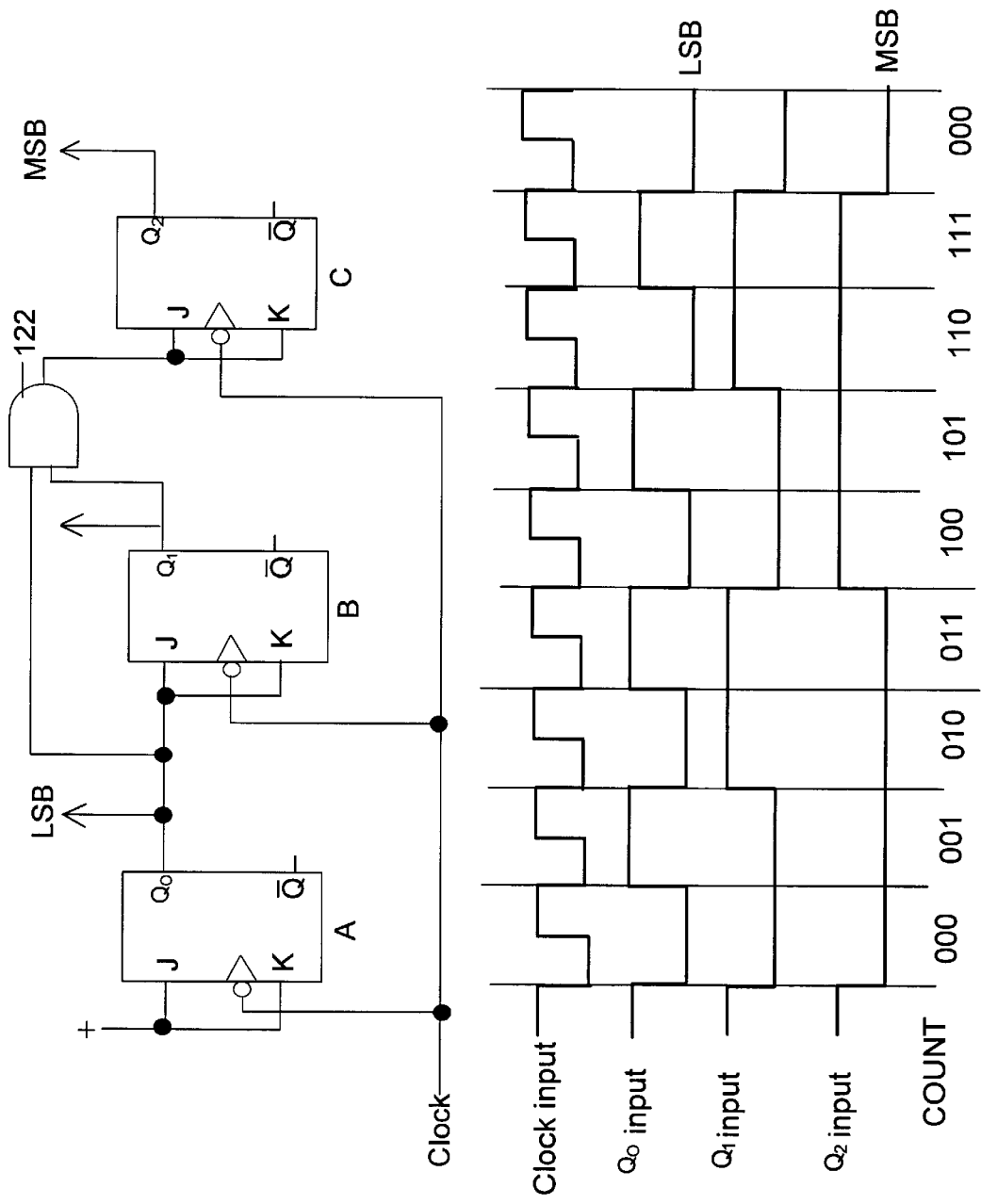

Standard counters of the type shown with logic diagrams in FIGS. 13A and 13B may be used. The example shown in FIG. 13A is of a four bit counter consisting of four T flip-flops. The example shown in FIG. 13B is of a synchronous up-counter with 3 J-K flip flops, and the bistables are master-slave JKs. The AND gate 122 is there to detect the movement when the output of the first two bistables is at logic 1. This detects a binary count of 11 and sends a signal to switch on the next bistable to give the next count as $100_2$. This is also shown in the timing diagram at the bottom half of the figure. These synchronous counters can be easily extended by adding more bistables for a higher count.

Once the prepackaged/predetermined logic state is activated by the logic and control circuit 102, as shown in FIG. 11, the pulse generation and amplification circuit 106 deliver the appropriate electrical pulses to the vagus nerve 54 of the patient 30 via an output buffer 108. The delivery of output pulses is configured such that the distal electrode 61 (electrode closer to the brain) is the cathode and the proximal electrode 62 is the anode. Timing signals for the logic and control circuit 102 of the pulse generator 70 are provided by a crystal oscillator 104. The battery 86 of the pulse generator 70 has terminals connected to the input of a voltage regulator 94. The regulator 94 smoothes the battery output and supplies power to the internal components of the pulse generator 70. A microprocessor 100 controls the program parameters of the device, such as the voltage, pulse width, frequency of pulses, on-time and off-time. The microprocessor may be a commercially available, general purpose microprocessor or microcontroller, or may be a custom integrated circuit device augmented by standard RAM/ROM components.

In the presently preferred embodiment, there are four stimulation states. A larger (or lower) number of states can be achieved using the same methodology, and such is considered within the scope of the invention. These four states are, LOW stimulation state, LOW-MED stimulation state, MED stimulation state, and HIGH stimulation state. Examples of stimulation parameters (delivered to the vagus nerve) for each state are as follows, LOW stimulation state example is,

| | |
|---|---|
| Current output: | 1.5 milliAmps. |
| Pulse width: | 0.20 msec. |
| Pulse frequency: | 20 Hz |
| Cycles: | 20 sec. on-time and 2.0 min. off-time in repeating cycles. |

LOW-MED stimulation state example is,

| | |
|---|---|
| Current output: | 2.0 milliAmps, |
| Pulse width: | 0.30 msec. |

-continued

| | |
|---|---|
| Pulse frequency: | 25 Hz |
| Cycles: | 1.5 min. on-time and 20.0 min. off-time in repeating cycles. |
| | MED stimulation state example is, |
| Current output: | 2.5 milliAmps. |
| Pulse width: | 0.30 msec. |
| Pulse frequency: | 30 Hz |
| Cycles: | 1.5 min. on-time and 20.0 min. off-time in repeating cycles. |
| | HIGH stimulation state example is, |
| Current output: | 3.5 milliAmps, |
| Pulse width: | 0.40 msec. |
| Pulse frequency: | 30 Hz |
| Cycles: | 2.0 min. on-time and 20.0 min. off-time in repeating cycles. |

These prepackaged/predetermined programs are mearly examples, and the actual stimulation parameters may deviate somewhat from these depending on the treatment application.

It will be readily apparent to one skilled in the art, that other schemes can be used for the same purpose. For example, instead of placing the magnet 82 on the pulse generator 70 for a prolonged period of time, different stimulation states can be encoded by the sequence of magnet applications. Accordingly, in an alternative embodiment there can be three logic states, OFF, LOW Stimulation (LS) state, and HIGH Stimulation (HS) state. Each logic state again corresponds to a prepackaged/predetermined program such as presented above. In such an embodiment, the system could be configured such that one application of the magnet triggers the generator into LS State. If the generator is already in the LS state then one application triggers the device into OFF State. Two successive magnet applications triggers the generator into MED stimulation state, and three successive magnet applications triggers the pulse generator in the HIGH Stimulation State. Subsequently, one application of the magnet while the device is in any stimulation state, triggers the device OFF.

Figure 14:
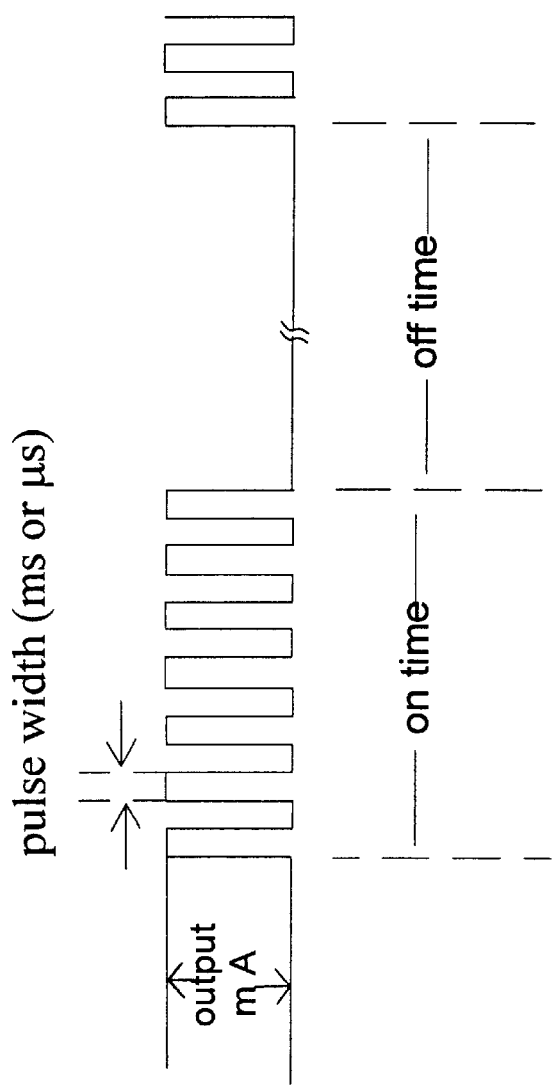
FIG. 14 shows the pulse train to be transmitted by the implant unit.
Figure 15:
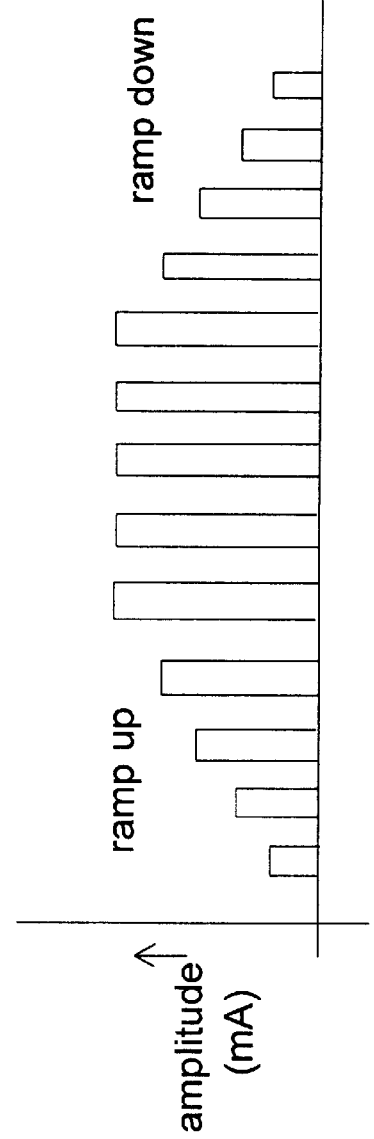
FIG. 15 shows the ramp-up and ramp-down characteristic of the pulse train.

The waveform of pulses delivered to the nerve tissue for stimulation therapy are shown graphically in FIG. 14. As shown in FIG. 15, for patient comfort when the electrical stimulation is turned on, the system is configured to deliver electrical stimulation in ramping up and ramping down format, instead of abrupt delivery of electrical pulses.

Figure 16:
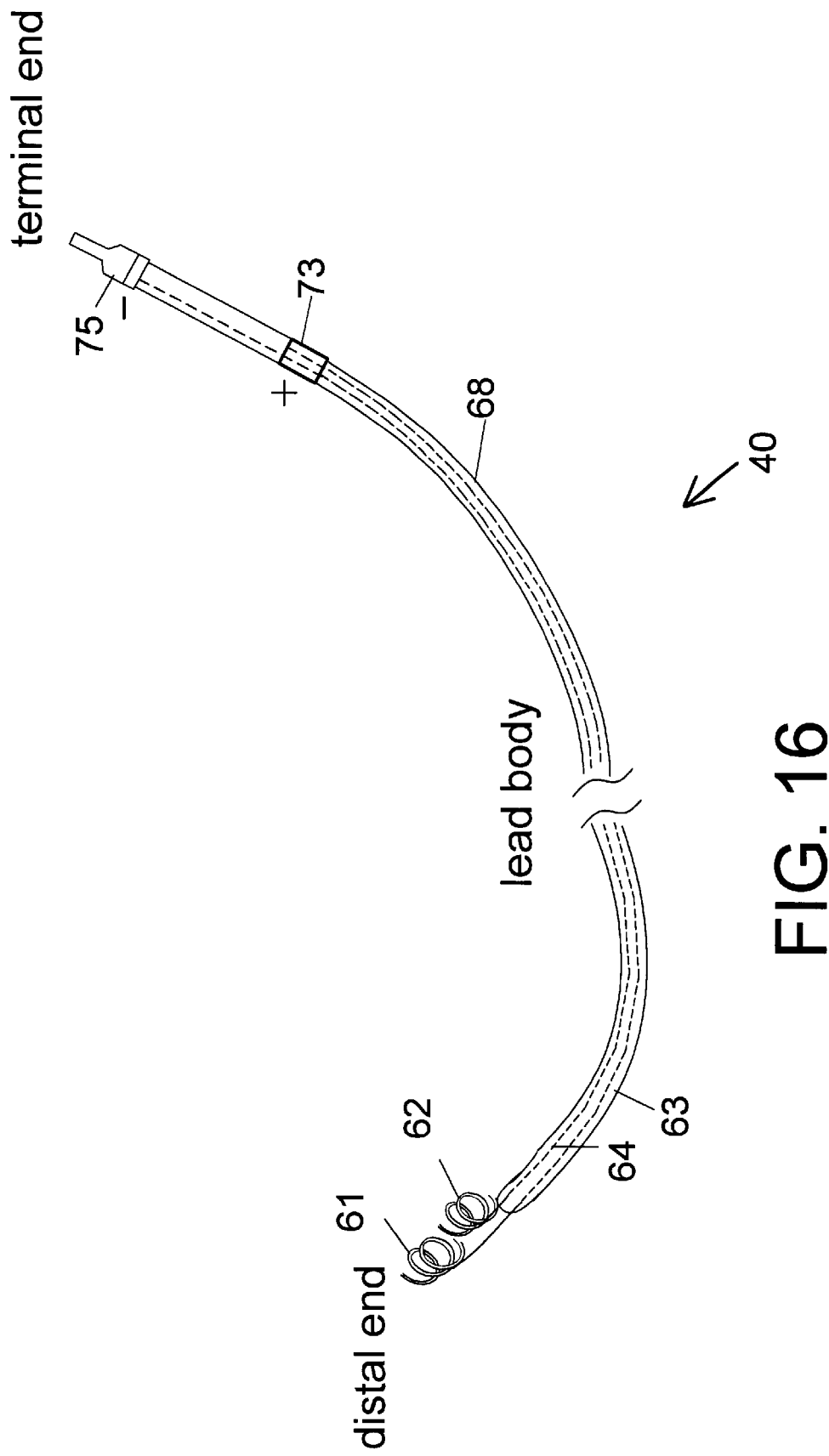
FIG. 16 is a schematic diagram of the implantable lead.

Reffering now to FIG. 16, the implanted lead component of the system is similar to cardiac pacemaker leads, except for distal portion of the lead. The lead terminal may be a linear bipolar or bifurcated, and plug(s) into the cavity of the pulse generator. The lead body insulation may be constructed of polyurethane, medical grade silicone, or silicone reinforced with polytetrafluoro-ethylene (PTFE). The electrodes for stimulating the vagus nerve may either wrap around the nerve once or may be spiral shaped. These stimulating electrodes may be made of pure platinum, platinum/Iridium alloy or platinum/iridium coated with titanium nitride. The conductor connecting the terminal to the electrodes is made of an alloy of nickel-cobalt. The implanted lead design variables are also summarized in the table below.

Table of lead design variables

| Proximal End Lead Terminal | Lead body-Insulation Materials | Lead-Coating | Conductor (connecting proximal and distal ends) | Electrode-Material | Distal End Electrode-Type |
|---|---|---|---|---|---|
| Linear Bipolar | Polyurethane | Antimicrobial coating | Alloy of Nickel-Cobalt | Pure Platinum | Spiral electrode |
| Bifurcated | Silicone | Anti-Inflamatory coating | | Platinum-Iridium (Pt/IR) Alloy | Wrap-around electrode |
| | Silicone with Polytetrafluoro-ethylene (PTFE) | Lubricious coating | | Pt/Ir coated with Titanium Nitride | Steroid eluting |
| | | | | Carbon | |

Once the lead is fabricated, coating such as antimicrobial, anti-inflammatory, or lubricious coating may be applied to the body of the lead.

What is claimed is:

1. An apparatus for providing neuromodulation therapy for at least one of epilepsy, dementia including Alzheimer's disease, obesity, eating disorders, coma, neurogenic/psychogenic pain, depression, sleep disorders, anxiety disorders, obsessive compulsive disorders and diabetes, comprising:

an implantable pulse generator; wherein said implantable pulse generator comprises microprocessor based circuitry and memory;

at least two predetermined/pre-packaged programs of said neuromodulation therapy stored in said memory to control pulses emitted by said implantable pulse generator, wherein said predetermined/pre-packaged programs define neuromodulation parameters of pulse amplitude, pulse-width, pulse frequency, on-time and off-time;

an implantable lead in electrical contact with said implantable pulse generator and having at least one electrode adapted to be in contact with a cranial nerve;

an external magnet; and means for selectively choosing between said at least two predetermined/pre-packaged programs with said external magnet to provide a selected predetermined/pre-packaged program and for activating said selected program for said neuromodulation therapy.

2. The apparatus of claim 1, wherein said cranial nerve is left vagus nerve.

3. The apparatus of claim 1, wherein said implantable pulse generator is operable without an external computer based programmer for programming.

4. A method of providing neuromodulation therapy for one of epilepsy, dementia including Alzheimer's disease, obesity, coma, migraines, severe depression, diabetes, neurogenic/psychogenic pain, anxiety disorders, sleep disorders, compulsive eating disorders, and obsessive compulsive disorders, using an implantable pulse generator system, said method comprising the steps of:

providing an implantable pulse generator; wherein said implantable pulse generator comprises microprocessor based circuitry and memory;

providing at least two predetermined/pre-packaged programs of said neuromodulation therapy stored in said memory to control pulses emitted by said implantable pulse generator, wherein said predetermined/pre-packaged programs define neuromodulation parameters of pulse amplitude, pulse-width, pulse frequency, on-time and off-time;

providing an implantable lead in electrical contact with said implantable pulse generator and having at least one electrode adapted to be in contact with a cranial nerve;

providing an external magnet; and selectively choosing between of said at least two predetermined/pre-packaged programs with said external magnet to provide a selected predetermined/pre-packaged program and activating said selected program for said neuromodulation therapy.

5. The method of claim 4, wherein said cranial nerves is the left vagus nerve.

6. The method of claim 4, wherein said implantable pulse generator does not require a computer based external programmer for programming.

7. An apparatus for providing electric pulses to a nerve tissue to provide stimulation therapy for at least one of epilepsy, dementia including Alzheimer's disease, obesity, eating disorders, coma, neurogenic/psychogenic pain, depression, sleep disorders, anxiety disorders, obsessive compulsive disorders, and diabetes, comprising:

an implantable pulse generator comprising microprocessor based circuitry and memory, wherein said implantable pulse generator is designed to operate without a computer based external programmer;

at least two predetermined/pre-packaged programs of said stimulation therapy stored in said memory to control said electrical pulses emitted by said implantable pulse generator wherein said predetermined/pre-packaged programs define neuromodulation parameters of pulse amplitude, pulse-width, pulse frequency, on-time and off-time;

an implantable lead in electrical contact with said implantable pulse generator and having at least one electrode adapted to be in contact with said nerve tissue; and external magnet means for selectively choosing between said at least two predetermined/pre-packaged programs with an external magnet to provide a selected predetermined/pre-packaged program and for activating said selected program for said neuromodulation therapy.

8. The apparatus of claim 7, wherein said nerve tissue is left vagus nerve.

9. The apparatus of claim 7, wherein said electrical pulse compromises at least one variable component selected from a group consisting of current amplitude, pulse width, pulse frequency, on-time, and off time.

10. The apparatus of claim 7, wherein at least two predetermined/pre-packaged programs control the variable components of said pulses.

11. A method for providing electric pulses to a nerve tissue to provide stimulation therapy for at least one of epilepsy, dementia including Alzheimer's disease, obesity, eating disorders, coma, neurogenic/psychogenic pain, depression, sleep disorders, anxiety disorders, obsessive compulsive disorders and diabetes, comprising the steps of:

providing an implantable pulse generator comprising microprocessor based circuitry and memory wherein said implantable pulse generator designed to operate without a computer based external programmer;

providing at least two predetermined/pre-packaged programs said stimulation therapy are stored in said memory to control said electrical pulses emitted by said implantable pulse generator wherein said predetermined/pre-packaged programs define neuromodulation parameter pulse amplitude, pulse-width, pulse frequency, on-time and off-time;

providing an implantable lead in electrical contact with said implantable pulse generator and having at least one electrode adapted to be in contact with said nerve tissue, and providing a means for selectively choosing between said at least two predetermined/pre-packaged programs with an external magnet to provide a selected predetermined/pre-packaged program and for activating said selected program for said neuromodulation therapy.

12. The method of claim 11, wherein said nerve tissue is left vagus nerve.

13. The method of claim 11, wherein said electrical pulse compromises at least one variable component selected from a group consisting of current amplitude, pulse width, pulse frequency, on-time, and off time.

14. The method of claim 11, wherein at least two predetermined/pre-packaged programs control the variable components of said pulses.

* * * * *